United States Patent [19]
Venturelli et al.

[11] Patent Number: 5,626,603
[45] Date of Patent: May 6, 1997

[54] HYDRAULIC STENT INSERTER

[75] Inventors: Luigi Venturelli, Concesio, Italy; Giancarlo Biamino, Berlin, Germany

[73] Assignee: Fogazzi Di Ventureli Andrea & C. S.n.c., Concesio, Italy

[21] Appl. No.: 538,551

[22] Filed: Oct. 3, 1995

[30] Foreign Application Priority Data

Oct. 5, 1994 [IT] Italy ................ BS94A0115

[51] Int. Cl.⁶ .................................................. A61M 25/00
[52] U.S. Cl. ...................... 606/198; 604/96; 606/191; 606/108
[58] Field of Search ................ 606/191, 192, 606/194, 198, 108; 604/96

[56] References Cited

U.S. PATENT DOCUMENTS 5,256,144  10/1993  Kraus et al. ................ 604/96
5,445,646   8/1995  Euteneuer et al. ........... 606/198

*Primary Examiner*—Michael Powell Buiz
*Assistant Examiner*—Patrick W. Rasche
*Attorney, Agent, or Firm*—McGlew and Tuttle

[57] ABSTRACT

The present invention pertains to an instrument to insert stents into arterial ducts in which a coaxial hose and sheath together, adjacent to a push rod, define a housing (27) designed to receive the stent (28) and the sheath slides longitudinally with respect to the hose due to the thrust of a fluid pressurized in a chamber (22) with closed ends between the hose and the sheath behind the housing of the stent, the movement of the sheath with respect to the hose causing the stent to be released.

10 Claims, 2 Drawing Sheets

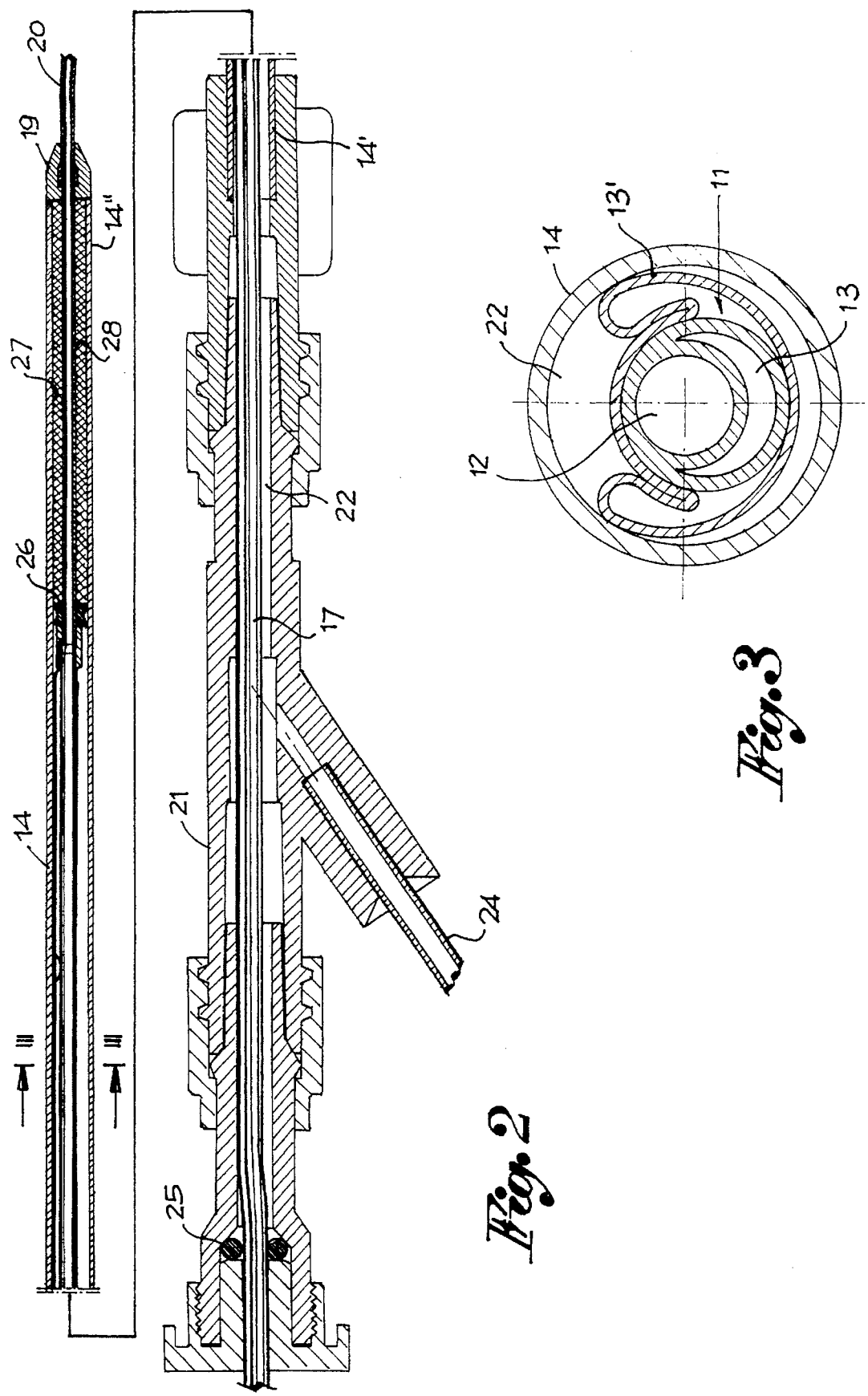

HYDRAULIC STENT INSERTER

FIELD OF THE INVENTION

The present invention pertains generally to an instrument to insert stents into arterial ducts.

BACKGROUND OF THE INVENTION

Stents are essentially metal armatures which are inserted without surgery into arteries as bypasses against the development of intimal hyperplasia, angiopathy occlusions and other disorders affecting arterial ducts. These armatures may be lattice elements in a metal alloy with a thermal memory, ie. in shape, and are flexible, strong, biocompatible, self-expanding, radio-opaque, and able to regain their shape even when overextended.

To be used, a stent with shape memory is first tightened and closed, at a low temperature, in a sheath with such dimensions as to be able to pass into an arterial duct. Then, once introduced into the artery, it is released and, with the body temperature, it regains its original shape.

Mechanical-expansion metal armatures are likewise known foe implantation in arterial ducts.

Such armatures, once taken in their contracted form into the desired section of an artery, are expanded, for example, by means of an inflatable ball inserted into the duct along with the armature.

However, though the above mentioned type of stent is available, a reliable technique for inserting it into the arterial duct has not yet been established. At present, to insert a stent into an arterial duct, catheters of a conventional type for arterial treatment and exploration are used. The stent is placed and tightened in a sheath, arranged inside the insertion catheter, carried with this to the area of implantation in an artery and mechanically released by pushing it out of the sheath with a thread extending into the catheter. This technique has however problems of insertion, due to the necessary force which is difficult to transmit over a distance with a flexible hose.

SUMMARY AND OBJECTS OF THE INVENTION

It is a primary object of the present invention to obviate such difficulties by providing a safer and more reliable stent inserter which is simple and handy to use.

It is another object of this invention to provide a stent inserter with a hydraulic action able to work always by traction and to more effectively implant the stent and extract the sheath.

It is yet another object of this invention to propose a stent inserter which integrates with a catheter for treating or exploring arterial ducts.

According to the invention, an instrument for inserting stents into arterial ducts is provided. The instrument includes a flexible hose with one or more openings wherein the hose has a proximal end and one distal end.

A flexible sheath is placed around the hose and the sheath also has a proximal end and a distal end. A union connection element is applied to the proximal end of the hose. The union element is designed to be provided with at least one coupling to insert at least one element into the hose. A push rod is fixed to the distal end of the hose. The push rod is suitable for connecting an additional extension hose, if necessary. The hose and the sheath together define a housing adjacent to the push rod. The housing is designed to receive the stent. The sheath slides longitudinally with respect to the hose due to the thrust of a pressurized fluid provided in a chamber. The chamber is disposed adjacent to the housing and is formed by two closed ends between the hose and the sheath, behind the housing and the stent. The movement of the sheath with respect to the hose causes the stent to be released.

An additional coupling is preferably provided which slides along the hose. The proximal end of the sheath is fixed to the additional coupling and the distal end of the sheath is opened adjacent to the push rod. The pressure chamber is defined between the hose and the sheath with a first seal which slides on the hose and is constrained by the inner surface of the additional coupling and on an opposite side with a second seal which is constrained to the hose and engaged sliding on the inner surface of the sheath. The second seal is adjacent to the housing for the stent. A syringe or pump is connected to the additional coupling to deliver fluid under pressure into the chamber to cause the sheath to go back on the hose if the hose is held in position or the hose goes forward in the sheath if the sheath is held in position, thus causing the stent to be released (causing the housing to open).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 2 shows a section of the inserter, at the elements forming a cylinder for hydraulic action; and FIG. 3 is a transversal cross-sectional view according to arrows III—III in FIG. 2.

DESCRIPTION OF THE PREFERRED EMBODIMENT

Figure 1:
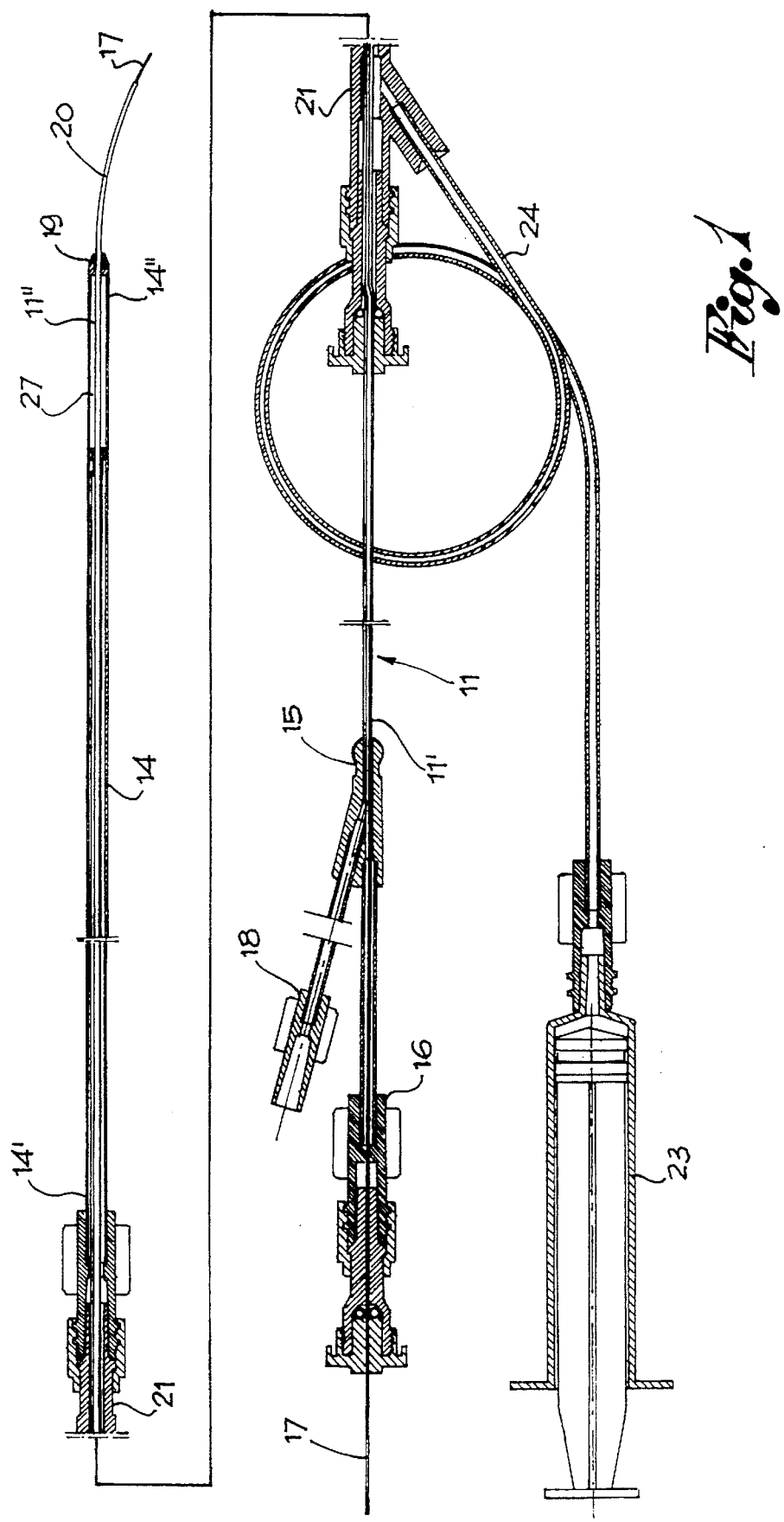
FIG. 1 shows a cross-sectional view of the whole assembly.

The inserter comprises a flexible hose 11 with two or more openings 12, 13, Which extends in an outer sheath 14 also flexible. The hose 11 has one proximal end 11' and one distal end 11". The proximal end 11' of the hose is fixed to a union 15 which may be provided with a first coupling 16, to insert a guiding thread 17 or another element in a first opening 12 of the hose, and with a second coupling 18 for delivery of a fluid into the second opening 13 to inflate a distal ball 13'. The union 15 and the couplings 16, 18 are in themselves known and entirely similar to those of conventional catheters for exploration or treatment in arteries. At the distal end 11' of the hose 11 a conical push rod 19 is applied which may also be connected to a tubular element 20, where required, so as to extend the hose and to get a thread guide 17 even beyond the push rod 19. Optic fibres or another system which shall extend to the push rod or beyond may pass into the hose in place of the thread 17.

An additional coupling 21 able to slide on the hose is coaxially provided along the hose 11.

The sheath 14 around the hose 11 has one proximal end 14' fixed to the additional coupling 21 and one open distal and 14" adjacent to the push rod.

The hose 11, with the additional coupling 21 for one section and with the outer sheath 14 for the remaining section, defines a duct or chamber 22 designed to receive a hydraulic fluid from a syringe 23 or from a pump (a hydraulic actuator or device for supplying a hydraulic fluid) connected to the additional coupling 21 by means of channel 24 which opens laterally into said duct or chamber 22.

This chamber 22 has its ends hermetically sealed in areas upstream and downstream of the hydraulic fluid inlet. More specifically, the chamber 22 is closed at the level of the additional coupling 21 by a first seal 25 slidingly provided on the hose 11 and engaged with the internal surface of the coupling and close to the distal end 14" of the sheath 14, by a second sheath 26 blocked on the hose and slidingly engaged with the inner surface of the sheath. Between this second sheath 26 and the push rod 19, the hose 11 and the outer sheath 14 define a housing 27 designed to receive a stent 28 to be inserted into an artery. The stent may be either of the type with shape memory or of mechanical expansion type, in its turn covered or otherwise with a biocompatible material.

When the stent is contracted into its smallest size it is inserted into the housing 27 through the open distal end 14" of the sheath 14 so as to be located between the second seal 26 and the open distal 14".

The instrument can therefore be introduced into the artery concerned so as to take the stent 28 into the implantation area. The push rod 19, as well as helping the instrument to advance, masks the stent so it does not get into contact with and damage the artery wall.

On reaching the stent implantation area, with the syringe 23 or the pump, a liquid is sent into the chamber 22 between the first seal 25 and the second seal 26. Then, keeping the hose 11 still by hand, and through this the push rod 19 and the second seal 26, the pressure of the liquid in the chamber 22 causes the sheath 14 to slide longitudinally since the thrust of the liquid on the first seal 25, sliding on the hose, forces the additional coupling 21, to which the proximal end of the sheath 14 is fixed, to withdraw on the hose.

In other words, the second seal 26 constrained to the hose 11 blocks the stent 28 thus preventing all withdrawal while the sheath 14 slides on the second seal withdrawing so far as to release the stent 28. This self-expands, if it is the type with shape memory, allowing the push rod to pass backwards and therefore the instrument to be withdrawn once the operation has been completed. On the other hand, if the stent is the mechanical expansion type, the instrument will be equipped with an inflatable ball with a fluid fed through the second opening 13 of the hose and which, acting on the inside of the stent, will cause the stent to expand for its implantation in situ in the artery.

A similar result is achieved by keeping the additional coupling 21 still and with it the outer sheath 14, and leaving the hose 11 free. In this case, the hose and the second seal will slide forwards in the sheath so as to expel the stent from the sheath.

Finally, it should be noted that the hose and/or the outer sheath may be strengthened by inserting metal or synthetic wires in order to give one and/or the other the required strength for the use the instrument is destined for.

What is claimed is:

1. An instrument to insert stents into arterial ducts, comprising:

a flexible hose with a passage opening and having one hose proximal end and one hose distal end;

a flexible sheath placed around said hose, said sheath having one sheath proximal end and one sheath distal end;

a union applied on said hose proximal end of said hose and provided with a coupling to insert at least one element into said hose;

a push rod fixed to said hose distal end and forming hose extension connection means for connecting said hose to a hose extension;

housing means defined by said hose cooperating with said sheath, said housing means being positioned adjacent to said push rod;

a stent received in said housing; and a pressure chamber formed with closed ends, said pressure chamber being entirely disposed between said hose and said sheath, behind said housing and said stent, said sheath sliding longitudinally with respect to said hose due to thrust of fluid pressurized in said pressure chamber wherein said movement of the sheath with respect to the hose opens said housing causing said stent to be released.

2. An instrument according to claim 1, wherein an additional coupling is placed connected for sliding along said hose;

said sheath proximal end is fixed to said additional coupling and said distal end of said sheath is open at a location adjacent to said push rod;

said pressure chamber is closed, on one side, at the level of said additional coupling by a first seal which is slidable on said hose and constrained to the inner surface of said coupling and, on the opposite side, with a second seal constrained to the hose and engaged sliding on the inner surface of the sheath, said second seal being positioned adjacent to said housing; and a hydraulic actuator is connected to said additional coupling to deliver said fluid under pressure into said chamber for one of movement of said sheath relative to said hose, to open said housing, if said hose is held in position and for movement of said sheath relative to said hose, to close said housing, if said sheath is held in position, to release said stent.

3. An instrument according to claim 2, wherein said hydraulic actuator is one of a pump and a syringe.

4. An instrument according to claim 1, wherein only two passage openings are provided in said hose.

5. An instrument to insert stents into arterial ducts, comprising:

a flexible hose with a passage opening and having one hose proximal end and one hose distal end;

a flexible sheath placed around said hose, said sheath having one sheath proximal end and one sheath distal end;

a union applied on said hose proximal end of the hose and provided with a coupling to insert at least one element into said hose;

a push rod fixed to said hose distal end and forming hose extension connection means for connecting said hose to a hose extension;

a stent;

housing means defined by said hose cooperating with said sheath, said housing means being disposed adjacent to said push rod for holding said stent;

a pressure chamber formed between a first seal and a second seal adjacent to said housing, said pressure chamber being entirely disposed between said hose and said sheath, said sheath sliding longitudinally with respect to said hose due to thrust of fluid pressurized in said pressure chamber wherein said movement of the sheath with respect to the hose opens said housing causing said stent to be released.

6. An instrument according to claim 5, further comprising an additional coupling connected for sliding along said hose with said sheath proximal end fixed to said additional coupling and said distal end of said sheath being open at a location adjacent to said push rod, said first seal being slidable on said hose and constrained to an inner surface of said coupling and, on the opposite side of said pressure chamber, said second seal being constrained to said hose and engaged sliding on an inner surface of the sheath, said second seal being positioned adjacent to said housing.

7. An instrument according to claim 5, further comprising:

a hydraulic actuator connected to said additional coupling to deliver said fluid under pressure into said pressure chamber for one of movement of said sheath relative to said hose, to open said housing, if said hose is held in position, and for movement of said sheath relative to said hose, to open said housing, if said sheath is held in position, to release said stent.

8. An instrument according to claim 7, wherein said hydraulic actuator is one of a pump and a syringe.

9. An instrument according to claim 5, wherein only two passage openings are provided in said hose.

10. An instrument to insert stents into arterial ducts, comprising:

a flexible hose with a passage opening and having one hose proximal end and one hose distal end;

a flexible sheath placed around said hose, said sheath having one sheath proximal end and one sheath distal end;

a union applied on said hose proximal end of the hose and provided with a coupling to insert at least one element into said hose;

a push rod fixed to said hose distal end and forming hose extension connection means for connecting said hose to a hose extension;

a stent;

housing means defined by said hose cooperating with said sheath, said housing means being disposed adjacent to said push rod for holding said stent;

a pressure chamber formed between a first seal and a second seal adjacent to said housing, said pressure chamber being entirely disposed between said hose and said sheath, said first seal being fixed relative to said sheath and moveable relative to said hose, said second seal being fixed relative to said hose and moveable relative to said sheath, said sheath sliding longitudinally with respect to said hose due to thrust of fluid pressurized in said pressure chamber wherein said movement of the sheath with respect to the hose opens said housing causing said stent to be released.

* * * * *